(12) United States Patent
Ito et al.

(10) Patent No.: US 8,771,488 B2
(45) Date of Patent: Jul. 8, 2014

(54) GAS SENSOR

(75) Inventors: Tetsuya Ito, Konan (JP); Satoshi Teramoto, Nisshin (JP); Kentaro Mori, Inuyama (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 13/565,040

(22) Filed: Aug. 2, 2012

(65) Prior Publication Data

US 2013/0032480 A1 Feb. 7, 2013

(30) Foreign Application Priority Data

Aug. 2, 2011 (JP) .................................. 2011-169070
Jun. 4, 2012 (JP) .................................. 2012-126737

(51) Int. Cl.
*G01N 27/419* (2006.01)
*G01N 27/406* (2006.01)
*G01N 27/409* (2006.01)
*G01N 27/407* (2006.01)

(52) U.S. Cl.
CPC .......... *G01N 27/406* (2013.01); *G01N 27/4062* (2013.01); *G01N 27/409* (2013.01); *G01N 27/407* (2013.01)
USPC ........... 204/424; 204/425; 204/426; 204/427; 204/428; 204/429; 73/23.31; 73/23.32

(58) Field of Classification Search
CPC ............. G01N 27/406; G01N 27/4062; G01N 27/409; G01N 27/407
USPC ..................... 204/424–429; 73/23.31–23.32
See application file for complete search history.

(56) References Cited

U.S. PATENT DOCUMENTS

| 4,645,572 | A | * | 2/1987 | Nishizawa et al. | 205/784 |
| 5,169,513 | A | * | 12/1992 | Mase et al. | 204/429 |
| 5,236,569 | A | * | 8/1993 | Murase et al. | 204/412 |
| 6,579,436 | B2 | * | 6/2003 | Wang et al. | 204/425 |
| 2004/0101740 | A1 | * | 5/2004 | Sanders | 429/40 |

FOREIGN PATENT DOCUMENTS

JP 2002-243700 A 8/2002

* cited by examiner

*Primary Examiner* — Bach Dinh
(74) *Attorney, Agent, or Firm* — Sughrue Mion, PLLC

(57) ABSTRACT

A gas sensor (100) includes an oxygen pump cell (135) and an oxygen-concentration detection cell (150) laminated together with a spacer (145) interposed therebetween. The spacer (145) has a gas detection chamber (145*c*) which faces electrodes (137, 152) of the cells (135, 150). The oxygen-concentration detection cell (150) produces an output voltage corresponding to the concentration of oxygen in the gas detection chamber (145*c*). The oxygen pump cell (135) pumps oxygen into and out of the measurement chamber (145*c*) such that the output voltage of the oxygen-concentration detection cell (150) becomes equal to a predetermined target voltage. A leakage portion mainly formed of zirconia is disposed between which electrically connects the oxygen-concentration detection cell (150) and the oxygen pump cell (135).

3 Claims, 10 Drawing Sheets

GAS SENSOR

BACKGROUND OF THE INVENTION

1. Field of the Invention

The present invention relates to a gas sensor.

2. Description of Related Art

An example of known gas sensors for detecting a specific gas is an oxygen sensor which includes a cell having a pair of electrodes disposed on the outer surface of a solid electrolyte member and which measures the air-fuel ratio of air-fuel mixture supplied to an internal combustion engine (hereinafter referred to as the air-fuel ratio of the internal combustion engine). Particularly, a laminate-type gas sensor is known in which two cells are stacked or laminated with a measurement chamber formed therebetween, and which is adapted to detect the concentration of oxygen contained in exhaust gas over the full range of the air-fuel ratio of the internal combustion engine (see Patent Document 1 below, etc.). In the laminate-type gas sensor, a first cell (also called an "oxygen-concentration detection cell") outputs to an external control circuit a voltage corresponding to the concentration of oxygen within the measurement chamber, and a second cell (also called an "oxygen pump cell") pumps oxygen out of the measurement chamber or pumps oxygen into the measurement chamber in accordance with a current supplied from the control circuit.

As described in Patent Document 1, such a laminate-type gas sensor is usually driven by a control circuit which feedback-controls the current supplied to the oxygen pump cell (hereinafter also referred to as the "pump current") on the basis of the output voltage of the oxygen-concentration detection cell. However, such a laminate-type gas sensor has a drawback. Namely, when the pump current of the oxygen pump cell is changed, the output voltage of the oxygen-concentration detection cell may fail to follow the change in the pump current and may change in accordance with a time lag. When the time lag becomes excessively large, the control circuit oscillates and the sensor output fluctuates, which makes stable measurement difficult and lowers measurement accuracy.

In order to overcome the above-mentioned drawback, according to the technique described in Patent Document 1, a high pass filter composed of a resistor and a capacitor is provided in the control circuit. This configuration prevents oscillation of the control circuit and prevents the output voltage of the oxygen-concentration detection cell from being greatly affected by a change in the pump current of the oxygen pump cell.

[Patent Document 1] Japanese Patent Application Laid-Open (kokai) No. 2002-243700

As described above, a dedicated control circuit including a high pass filter composed of a resistor and a capacitor as disclosed in Patent Document 1 has been conventionally used for a laminate-type gas sensor having two cells; i.e., an oxygen pump cell and an oxygen-concentration detection cell. This is because use of such a dedicated control circuit has been considered desirable. However, the use of such a dedicated control circuit may impair compatibility of the control circuit with a gas sensor of a type which does not cause the control circuit to oscillate and which avoids the necessity of providing a high pass filter in the control circuit. Also, since a resistor and a capacitor must be added in order to provide a high pass filter in the control circuit, the manufacturing cost may thereby increase.

SUMMARY OF THE INVENTION

It is therefore an object of the present invention to provide a technique for use in a gas sensor driven by feedback control which suppresses oscillation of a control circuit caused by the feedback control, even when a configuration for suppressing oscillation is not provided in the control circuit.

The present invention has been made to at least partially solve the above-described problems of the related art. More particularly, the above object of the present invention has been achieved by providing (1) a gas sensor comprising: a measurement chamber into which a gas to be measured can be introduced; an oxygen-concentration detection cell including a plate-shaped first solid electrolyte member and a pair of electrodes disposed on the first solid electrolyte member, the oxygen-concentration detection cell being disposed adjacent to the measurement chamber such that at least a portion of a first electrode which is one of the electrodes of the oxygen-concentration detection cell faces the measurement chamber, the oxygen-concentration detection cell producing an output voltage corresponding to the concentration of oxygen within the measurement chamber;

an oxygen pump cell including a plate-shaped second solid electrolyte member and a pair of electrodes disposed on the second solid electrolyte member, the oxygen pump cell being disposed adjacent to the measurement chamber such that the oxygen pump cell faces the oxygen-concentration detection cell through the measurement chamber and such that at least a portion of a second electrode which is one of the electrodes of the oxygen pump cell faces the measurement chamber, the oxygen pump cell pumping oxygen into the measurement chamber and pumping oxygen out of the measurement chamber in accordance with a pump current supplied to the oxygen pump cell such that the output voltage of the oxygen-concentration detection cell becomes equal to a predetermined target voltage; and an insulating layer in which the measurement chamber is provided and which is interposed between the first solid electrolyte member and the second solid electrolyte member so as to insulate the oxygen-concentration detection cell and the oxygen pump cell from each other, wherein a leakage portion which is mainly formed of zirconia and which electrically connects the oxygen-concentration detection cell to the oxygen pump cell is disposed between the oxygen-concentration detection cell and the oxygen pump cell such that the leakage portion is located adjacent to the insulating layer.

According to the above gas sensor (1) of the invention, since the two cells electrically communicate with each other through the leakage portion, a delay (phase delay) in change in the output voltage of the oxygen-concentration detection cell in relation to a change in the current of the oxygen pump cell is reduced. Accordingly, it is possible to suppress the occurrence of oscillation in feedback control performed by a control circuit which controls the current of the oxygen pump cell in accordance with a change in the output voltage of the oxygen-concentration detection cell. That is, when the pump current of the oxygen pump cell is changed, the above configuration prevents the output voltage of the oxygen-concentration detection cell from being greatly influenced, whereby fluctuation of the sensor output is suppressed. Notably, as used herein, the expression "electrically communicate" means that a path exists through which electrons and/or ions move.

Further, since the leakage portion is provided in the gas sensor, it is possible to suppress oscillation without preparing a dedicated control circuit which includes a constituent element for suppressing oscillation stemming from feedback control, such as a high pass filter including a resistor and a capacitor. Accordingly, it is possible to insure compatibility of the control circuit with a gas sensor which does not cause the control circuit to oscillate and which does not require a dedicated control circuit. In addition, since constituent elements, such as a resistor and a capacitor, for suppressing oscillation are not additionally provided in the control circuit, the manufacturing cost can be reduced.

Incidentally, in the above-described gas sensor (1) of the invention, the insulating layer, which insulates the oxygen-concentration detection cell and the oxygen pump cell from each other, is interposed between the oxygen-concentration detection cell and the oxygen pump cell. Further, the leakage portion, which electrically connects the oxygen-concentration detection cell and the oxygen pump cell, is provided separately from the insulating layer. Oscillation in feedback control can be suppressed by establishing electrical communication between the two cells. Therefore, the gas sensor may be configured such that electrical communication is established between the oxygen-concentration detection cell and the oxygen pump cell by interposing an electrical connection layer between the two cells without providing the insulating layer therebetween. However, if such a connection layer is provided, a large voltage (also referred to as "leakage voltage") is produced due to a current (also referred to as "leakage current") flowing between the two cells via the connection layer and is superimposed on the output voltage of the oxygen-concentration detection cell. As a result, the measurement accuracy of the gas sensor may decrease. In contrast, the gas sensor (1) of the invention is configured such that the insulating layer is interposed between the oxygen-concentration detection cell and the oxygen pump cell and the leakage portion is separately provided at a portion of the insulating layer. Therefore, superposition of a leakage voltage on the output voltage of the oxygen-concentration detection cell can be adequately suppressed. Accordingly, it is possible to suppress oscillation in feedback control, while preventing a decrease in measurement accuracy of the gas sensor due to the leakage current.

Notably, the leakage portion may be provided at a position which electrically connects the reference electrode or reference electrode lead of the oxygen-concentration detection cell and the oxygen pump cell by electrically connecting the first solid electrolyte member and the second solid electrolyte member, or at a position where the leakage portion electrically connects the outer electrode or outer electrode lead of the oxygen pump cell and the oxygen-concentration detection cell by electrically connecting the first solid electrolyte member and the second solid electrolyte member. The leakage portion is disposed such that it is located between the oxygen-concentration detection cell and the oxygen pump cell.

In a preferred embodiment (2), the above gas sensor (1) further comprises a plate-shaped heater which is laminated on the second solid electrolyte member and in which a heating portion is embedded, wherein the leakage portion is provided in a region which at least partially overlaps the heating portion as viewed in the lamination direction of the gas sensor.

According to the gas sensor (2), the leakage portion is disposed such that it overlaps a region where heating is performed by the heating element. Therefore, the temperature of the leakage portion is properly controlled, whereby the electrical conductivity of the zirconia which constitutes the leakage portion can be properly maintained. Accordingly, it is possible to more reliably suppress oscillation of feedback control and to prevent fluctuation of the sensor output.

In another preferred embodiment (3) of the gas sensor (1) or (2) above, the leakage portion penetrates a portion of the insulating layer in the lamination direction of the gas sensor, the leakage portion being sandwiched between the first solid electrolyte member and the second solid electrolyte member; and on at least one cross section of the insulating layer taken perpendicular to the lamination direction, the leakage portion has an area which is less than 50% the sum of the area of the insulating layer and the area of the leakage portion.

According to the above gas sensor (3), the occupation ratio of the leakage portion in relation to the insulating layer can be properly adjusted by making the area of the leakage portion smaller than 50% the sum of the area of the insulating layer and the area of the leakage portion (i.e., by making the area of the leakage portion smaller than the area of the insulating layer). Accordingly, oscillation in the feedback control is suppressed in a satisfactory manner by the leakage current, and the leakage voltage superimposed on the output voltage of the oxygen-concentration detection cell is adequately suppressed, whereby a reduction in measurement accuracy of the gas sensor is prevented due to the leakage voltage. Notably, it is sufficient for the leakage portion to have an area within the above-described range on only one of arbitrary cross sections of the insulating layer taken perpendicular to the lamination direction. Preferably, the leakage portion has an area within the above-described range on more than one of possible cross sections. More preferably, the leakage portion has an area within the above-described range on all the cross sections.

In yet another preferred embodiment (4) of the gas sensor of any one of (1) to (3) above, the outer surface of the leakage portion is covered by the oxygen pump cell, the oxygen-concentration detection cell and the insulating layer.

According to the gas sensor (4), the outer surface of the leakage portion can be prevented from exposure to exhaust gas. Thus, adhesion of carbon (soot) or a water droplet on the outer surface of the leakage portion can be suppressed. Accordingly, it is possible to prevent the occurrence of blackening of the gas sensor due to adhesion of carbon to the leakage portion and the generation of cracks in the gas sensor due to adhesion of water droplets to the leakage portion. The occurrence of blackening and the generation of cracks would otherwise result in a sensor failure.

Notably, the present invention can be practiced in various forms. For example, the present invention can be practiced in the form of a gas sensor, in the form of a gas detection apparatus including the gas sensor, or in the form of a vehicle or the like which includes the gas detection apparatus.

DESCRIPTION OF REFERENCE NUMERALS

Figure 1:
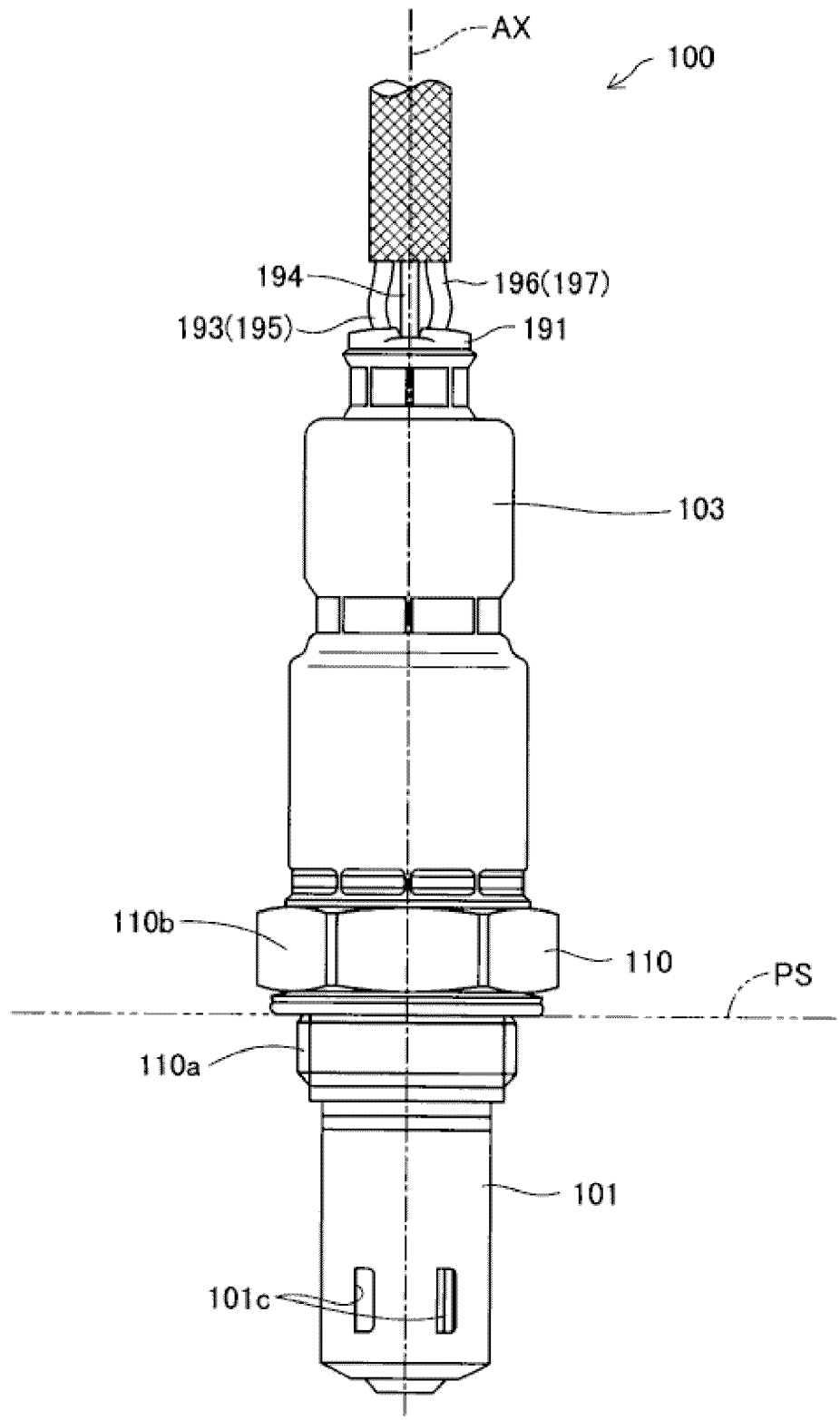
FIG. 1 is a schematic view showing the external view of a gas sensor.

Reference numerals used to identify various structural features in the drawings include the following.
11 to 18: First Through-hole Conductor
21, 22: Heater Through-hole Conductor
100, 100B, 100a: Gas Sensor
101: Protector
101c: Introduction Hole
103: Outer Sleeve
110: Metallic Shell
110c: Through-hole
110k: End portion
111: Step Portion
113: Ceramic Holder
113c: Through-hole
114: First Layer of Charged Powder
115: Second Layer of Charged Powder
116: Metal Cup
116c: Through-hole
117: Crimp Ring
120: Gas Sensor Element
120a: First Surface
120b: Second Surface
121: Gas Detection Section
125: First Electrode Pad (Ip electrode pad)
126: Second Electrode Pad (COM electrode pad)
127: Third Electrode Pad (Vs electrode pad)
128, 129: Heater Electrode Pad
130: Detection Element
131: Protection Layer
132: Porous Portion
135: Oxygen Pump Cell
136: Solid Electrolyte Member
136a, 136b: First Surface, Second Surface
137: Electrode
137L: Lead Portion
137M: Electrode Portion
138: Electrode
138L: Lead Portion
138M: Electrode Portion
139: Alumina Layer
145: Spacer
145c: Gas Detection Chamber
146: diffusion Limiting Portion
148: Leakage Portion
150: Oxygen-Concentration Detection Cell
151: Solid Electrolyte Member
151a, 151b: First Surface, Second Surface
152: Electrode
152L: Lead Portion
152M: Electrode Portion
153: Electrode
153L: Lead Portion
153M: Electrode Portion
154: Alumina Layer
160: Heater Element
161, 162: First and Second Insulating Members
163: Heating Resistor
164, 165: Heater Lead Portion
170: Ceramic Sleeve
170c: Axial Hole
181: Separator
181c: Through-hole
185 to 186: Connection Terminal
190: Urging Metal Piece
191: Grommet
193 to 197: Lead Eire
200, 200a: Control Circuit
210: PID Element
211: Operational Amplifier
221 to 223: Resistor
230: Reference Power Supply
240: High Pass filter
241: Resistor
242: Capacitor

DETAILED DESCRIPTION OF THE INVENTION

The invention will next be described in greater detail with reference to the drawings. However, the present invention should not be construed as being limited thereto.

A. First Exemplary Embodiment:

FIG. 1 is a schematic view showing the external view of a gas sensor 100 according to one embodiment of the present invention. In FIG. 1, the imaginary center axis AX of the gas sensor 100 (hereinafter also referred to as the "axis AX") is shown by an alternate long and short dashed line. This gas sensor 100 is a so-called full range air-fuel-ratio sensor which is attached to an exhaust pipe of an internal combustion engine or the like and linearly detects the concentration of oxygen contained in exhaust gas (gas to be measured) over a full range ranging from a rich region to a lean region.

The gas sensor 100 extends in the direction of the axis AX. The gas sensor 100 is fixedly attached to the outer surface of the exhaust pipe such that a front end portion (a lower end portion in FIG. 1) of the gas sensor 100 is inserted into the exhaust pipe, and a rear end portion (an upper end portion in FIG. 1) thereof projects outward from the exhaust pipe. In FIG. 1, the position of the outer surface of the exhaust pipe, to which the gas sensor 100 is attached, is indicated by an alternate long and two short dashed line PS.

The gas sensor 100 has a metallic shell 110 for fixedly attaching the gas sensor 100 to the exhaust pipe. The metallic shell 110 is a tubular metallic member having a through-hole 110c (see FIG. 2) extending in the direction of the axis AX. The metallic shell 110 has a thread portion 110a and a tool engagement portion 110b formed on the outer periphery of the metallic shell 110. The thread portion 110a meshes with a thread grove which is provided on the exhaust pipe for attachment of the gas sensor 100. When the gas sensor 100 is attached, a tool such as spanner or wrench is engaged with the tool engagement portion 110b.

A double wall tubular protector 101 with a bottom is fixed to the front end of the metallic shell 110 by laser welding. A plurality of introduction holes 101c are formed in each of the inner and outer walls of the double wall protector 101 in order to introduce exhaust gas into the interior of the double wall protector 101 when the gas sensor 100 is attached to the exhaust pipe.

A tubular metallic outer sleeve 103 is fixed to the rear end of the metallic shell 110 by laser welding. Three sensor lead wires 193, 194, 195 and two heater lead wires 196, 197 for electrically connecting the gas sensor 100 to an external control circuit 200 (see FIG. 5) are inserted into the gas sensor 100 through the rear end of the outer sleeve 103. A grommet 191, which is formed of fluororubber and is adapted to seal the interior of the outer sleeve 103, is attached to the rear end of the outer sleeve 103. The five lead wires 193 to 197 are inserted into the outer sleeve 103 through the grommet 191.

Figure 2:
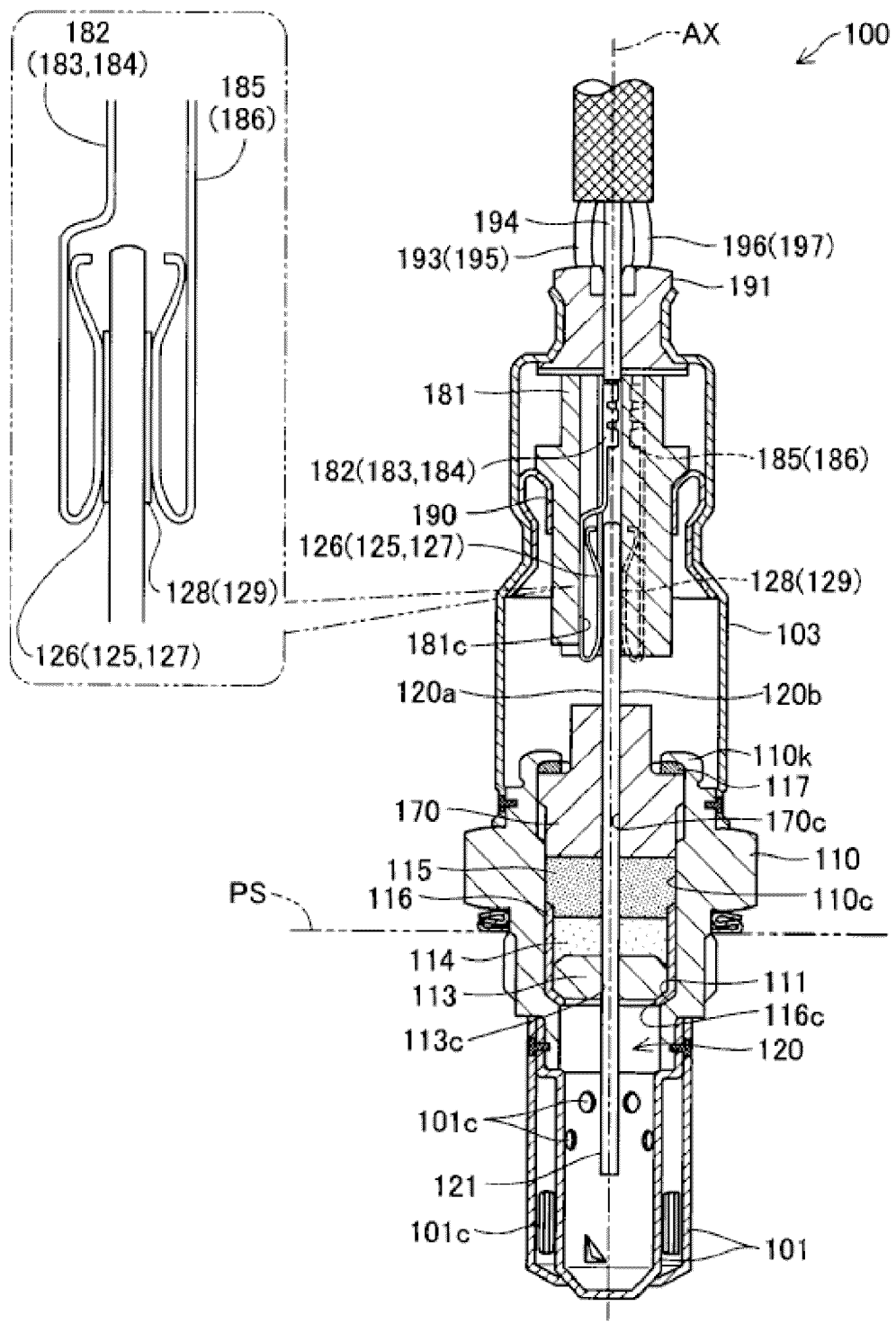
FIG. 2 is a schematic sectional view showing the internal structure of the gas sensor.

FIG. 2 is a schematic sectional view showing the internal structure of the gas sensor 100 as viewed from the same direction as the view direction of FIG. 1. Like FIG. 1, FIG. 2 includes an alternate long and short dashed line which represents the imaginary center axis AX of the gas sensor 100 and an alternate long and two short dashed line PS which represents the position of the outer surface of the exhaust pipe, to which the gas sensor 100 is attached.

The gas sensor 100 includes a gas sensor element 120 which outputs a signal corresponding to the concentration of oxygen. The gas sensor element 120 has a laminated structure including elongated plate members stacked or laminated together, and has the shape of a parallelepiped having an approximately rectangular cross section taken perpendicular to the imaginary center axis AX (the details are provided below). The gas sensor element 120 is fixedly held within the through-hole 110c of the metallic shell 110 such that the gas sensor element 120 extends in the direction of the axis AX within the gas sensor 100. In FIG. 2, first and second surfaces 120a, 120b of the gas sensor element 120, which face each other in the lamination direction thereof, face leftward and rightward, respectively, in FIG. 2.

A gas detection section 121 for detecting the concentration of oxygen contained in exhaust gas is provided at a front end portion (a lower end portion in FIG. 2) of the gas sensor element 120. The gas detection section 121 is accommodated and disposed within the protector 101. Therefore, when the gas sensor 100 is attached to the exhaust pipe, the gas detection section 121 is exposed to exhaust gas introduced through the introduction holes 101c.

A tubular insulating separator 181 having a through-hole 181c extending in the direction of the axis AX is fixedly held within the outer sleeve 103 provided on the rear end side (upper side in FIG. 2) of the metallic shell 110. Specifically, an urging metal piece 190 disposed around the separator 181 holds the separator 181 within the outer sleeve 103 in a state in which the separator 181 is urged toward the grommet 191. A rear end portion of the gas sensor element 120 is accommodated in the through-hole 181c of the separator 181.

The three sensor electrode pads 125, 126, 127 and the two heater electrode pads 128, 129 are provided on a rear end portion of the gas sensor element 120. Specifically, the three sensor electrode pads 125, 126 and 127 are disposed on the first surface 120a such that they are arranged in parallel in the direction perpendicular to the sheet of FIG. 2, and the two heater electrode pads 128, 129 are disposed on the second surface 120b such that they are arranged in parallel in the direction perpendicular to the sheet of FIG. 2. Three sensor connection terminals 182, 183, 184 and two heater connection terminals 185, 186 are provided in the through-hole 181c of the separator 181 such that they come into contact with the corresponding electrode pads 125 to 129 of the gas sensor element 120. The sensor connection terminals 182 to 186 are electrically connected to the five lead wires 193 to 197, which are inserted into the gas sensor 100 through the grommet 191.

On the left side of the sheet of FIG. 2, the state of contact between the electrode pads 125 to 129 of the gas sensor element 120 and the connection terminals 182 to 186 within the through-hole 181 c of the separator 181 is schematically shown. Each of the connection terminals 185 to 186 provided in the separator 181 is bent rearward at its end located on the side toward the front end of the gas sensor 100, and serves as a plate spring. Thus, the connection terminals 185 to 186 press the corresponding electrode pads 125 to 129 by their elastic forces. The details of the electrode pads 125 to 129 of the gas sensor element 120 are described below.

The gas sensor element 120 is fixedly held within the metallic shell 110 by the following structure provided within the metallic shell 110. A step portion 111 is provided at the front end side of the through-hole 110c of the metallic shell 110 such that the step portion 111 projects radially inward. A metal cup 116 having a through-hole 116c formed in the bottom wall thereof is disposed in the through-hole 110c of the metallic shell 110 such that a peripheral edge portion of the bottom wall of the metal cup 116 engages the step portion 111.

A ceramic holder 113 is disposed in inner space of the metal cup 116 to be located on the bottom side thereof. The ceramic holder 113 is formed of alumina ($Al_2O_3$), and has a rectangular through-hole 113c which is formed at the center of the ceramic holder 113 so as to enable the gas sensor element 120 to extend through the ceramic holder 113.

A first layer of charged powder 114 (talc) is formed within the metal cup 116 so as to gas-tightly hold the gas sensor element 120, which is passed through the through-hole 116c of the metal cup 116 and through-hole 113c of the ceramic holder 113. The first layer of charged powder 114 is formed by charging talc powder on the ceramic holder 113. Thus, the gas sensor element 120 is held within the through-hole 110c of the metallic shell 110 in a state in which the gas sensor element 120 is integrated with the metal cup 116, the ceramic holder 113, and the first layer of charged powder 114.

A second layer of charged powder 115 (talc) is also formed within the through-hole 110c of the metallic shell 110 by charging talc powder such that the second layer of charged powder 115 is located above the first layer of charged powder 114. The second layer of charged powder 115 provides a gastight seal between the rear end side of the metallic shell 110 and the gas detection section 121 of the gas sensor element 120. A ceramic sleeve 170 is disposed above the second layer of charged powder 115.

The ceramic sleeve 170 is a tubular body having a rectangular axial hole 170c which extends in the direction of the axis AX and through which the gas sensor element 120 is passed. The ceramic sleeve 170 may be formed of alumina. A rear end portion 110k of the metallic shell 110 is bent radially inward by crimping so as to fix the ceramic sleeve 170 to the metallic shell 110 in a state in which the ceramic sleeve 170 is pressed toward the second layer of charged powder 115. Notably, a crimp ring 117 is disposed between the rear end portion 110k of the metallic shell 110 and the ceramic sleeve 170.

Figure 3:
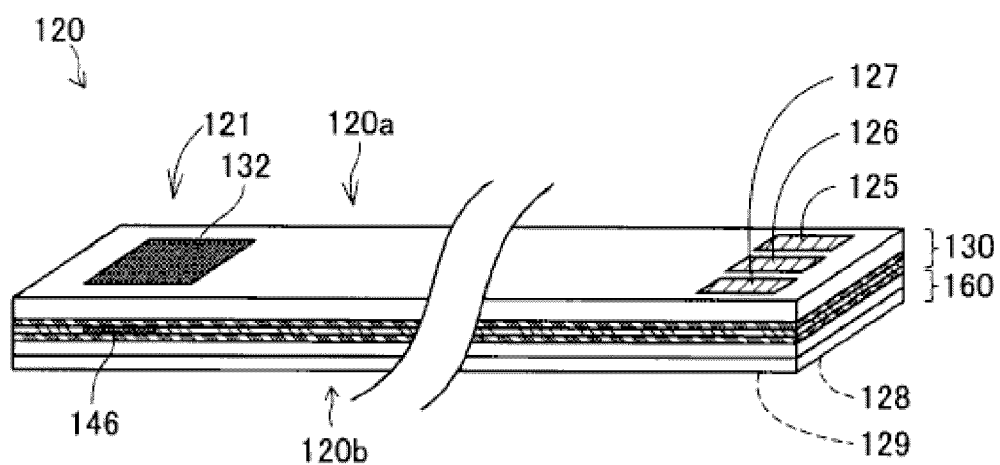
FIG. 3 is a schematic perspective view showing the structure of a gas sensor element.

FIG. 3 is a schematic perspective view showing the structure of the gas sensor element 120. In FIG. 3, the first surface 120a of the gas sensor element 120 faces upward, and the second surface 120b of the gas sensor element 120 faces downward. The direction of the axis AX (FIGS. 1 and 2) corresponds to the left-right direction in FIG. 3. The front end side corresponds to the left side in FIG. 3, and the rear end side corresponds to the right side in FIG. 3. The gas sensor element 120 includes a plate-shaped detection element 130 (located on the upper side in FIG. 3) and a plate-shaped heater element 160 (located on the lower side in FIG. 3) which are laminated and fired such that they are united together.

As described with reference to FIG. 2, the gas detection section 121 is formed on the front end side of the gas sensor element 120, and the three electrode pads 125 to 127 are disposed on the first surface 120a to be located on the rear end side thereof. Although not illustrated in FIG. 3, the two electrode pads 128, 129 are disposed on the second surface 120b to be located on the rear end side thereof.

Figure 4:
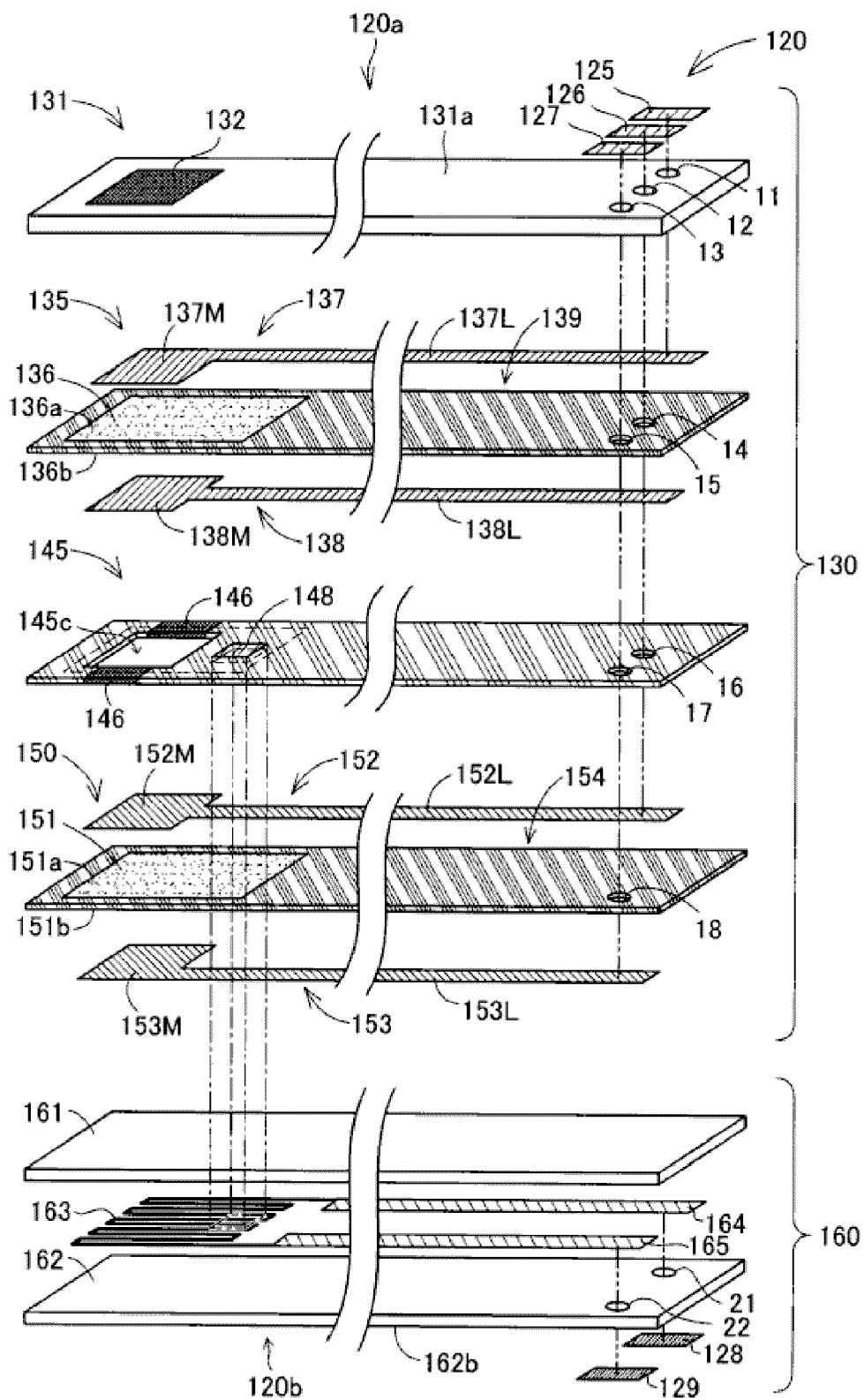
FIG. 4 is a schematic perspective view showing the gas sensor element in an exploded state.

FIG. 4 is a schematic perspective showing the gas sensor element 120 in an exploded state. In FIG. 4, the constituent elements of the gas sensor element 120 disassembled in the lamination direction (the vertical direction in FIG. 4) are illustrated, with the front ends of the constituent elements located on the left side of FIG. 4 and the rear ends of the constituent elements located on the right side of FIG. 4. Notably, alternate long and two short dashed lines in FIG. 4 show that the constituent elements connected by an alternate long and two short dashed line are electrically connected with each other. The detection element 130 of the gas sensor 100 includes a protection layer 131, an oxygen pump cell 135, a spacer 145, and an oxygen-concentration detection cell 150, which are stacked or laminated in this sequence from the first surface 120a side.

The protection layer 131 is a platelike member which is mainly formed of alumina, and protects the first surface 120a side of the gas sensor element 120. A porous portion 132 is formed in a front end portion of the protection layer 131. The porous portion 132 allows gas to flow therethrough in the lamination direction of the protection layer 131 (in the vertical direction in FIG. 4). The porous portion 132 is formed in a region which overlaps an electrode portion 137M, described below, when the gas sensor element 120 is viewed in the lamination direction. The porous portion 132 functions as a gas flow channel through which exhaust gas is pumped into the gas detection section 121 and pumped out from the gas detection section 121.

The three electrode pads 125 to 127 are disposed on a rear end portion of the outer surface 131a of the protection layer 131 such that they are arranged in parallel in the width direction of the gas sensor element 120 (the direction perpendicular to the sheet of FIG. 4). First to third through-hole conductors 11 to 13 are formed in the protection layer 131 at positions corresponding to the first to third electrode pads 125 to 127.

The oxygen pump cell 135 includes a solid electrolyte member 136, an alumina layer 139 in which the solid electrolyte member 136 is disposed, and a pair of electrodes 137, 138. The solid electrolyte member 136 is a platelike member which is mainly formed of zirconia ($ZrO_2$) and which has an area slightly greater than the pair of electrode portions 137M, 138M. The alumina layer 139 is a platelike member which is provided to surround the circumference of the solid electrolyte member 136 and covers the periphery thereof, and which has a size approximately the same as that of the protection layer 131. Fourth and fifth through-hole conductors 14, 15 are formed in a rear end portion of the alumina layer 139 and are electrically connected to the second and third through-hole conductors 12, 13, respectively, formed in the protection layer 131. The solid electrolyte member 136 of the oxygen pump cell 135 corresponds to the "second solid electrolyte member" of the invention.

The two electrodes 137, 138 respectively have porous electrode portions 137M, 138M mainly formed of platinum (Pt), and lead portions 137L, 138L. The electrode portions 137M, 138M are disposed on a first surface 136a (the upper surface in FIG. 4) and a second surface 136b (the lower surface in FIG. 4), respectively, of the solid electrolyte member 136. Of these electrode portions 137M, 138M, the electrode portion 138M disposed on the second surface 136b is exposed to a gas detection chamber 145c described below. Meanwhile, when the gas sensor 100 is attached to the exhaust pipe, the electrode portion 137M disposed on the first surface 136a is exposed to exhaust gas via the porous portion 132 of the protection layer 131. The electrode 138 corresponds to the "second electrode" of the invention.

The lead portions 137L, 138L extend rearward from the electrode portions 137M, 138M, respectively. Of these lead portions 137L, 138L, the lead portion 137L of the electrode 137 disposed on the first surface 136a is electrically connected to the first electrode pad 125 through the first through-hole conductor 11 of the protection layer 131. Meanwhile, the lead portion 138L of the electrode 138 disposed on the second surface 136b is electrically connected to the second electrode pad 126 through the fourth through-hole conductor 14 provided in the solid electrolyte member 136 and the second through-hole conductor 12 provided in the protection layer 131.

The spacer 145 is a plate-shaped insulating member which is mainly formed of alumina and which has a size approximately the same as that of the alumina layer 139 of the oxygen pump cell 135. An opening is formed in a front end portion of the spacer 145. When the spacer 145 is sandwiched between the oxygen pump cell 135 and the oxygen-concentration detection cell 150, the opening forms the gas detection chamber 145c into which exhaust gas (gas to be measured) is introduced. The spacer 145 corresponds to the "insulating layer" of the invention, and the gas detection chamber 145c corresponds to the "measurement chamber" of the invention.

Diffusion limiting portions 146 are formed in two side wall portions of the spacer 145 which face each other in the width direction of the spacer 145 through the opening. The diffusion limiting portions 146 are formed of porous alumina having gas permeability. In the gas sensor element 120, exhaust gas is introduced into the gas detection chamber 145c in an amount corresponding to the gas permeability of the diffusion limiting portions 146. That is, the diffusion limiting portions 146 serve as a gas introduction portion of the gas detection section 121.

A sixth through-hole conductor 16 is formed in a rear end portion of the spacer 145 and electrically connects to the lead portion 138L of the electrode 138 of the oxygen pump cell 135. Also, a seventh through-hole conductor 17 is formed adjacent to the sixth through-hole conductor 16 and electrically connects to the fifth through-hole conductor 15 provided in the alumina layer 139 of the oxygen pump cell 135.

The spacer 145 functions as an insulating layer which insulates the oxygen pump cell 135 and the oxygen-concentration detection cell 150 from each other. The spacer 145 has a leakage portion 148 which extends through the spacer 145 in the thickness direction and electrically connects the oxygen pump cell 135 and the oxygen-concentration detection cell 150. The leakage portion 145 is described in detail below.

The oxygen-concentration detection cell 150 includes a solid electrolyte member 151, an alumina layer 154 in which the solid electrolyte member 151 is disposed, and a pair of electrodes 152, 153. The solid electrolyte member 151 is a platelike member which is mainly formed of zirconia and which has an area slightly greater than the pair of electrode portions 152M, 153M. The alumina layer 154 is a platelike member which is provided to surround the circumference of the solid electrolyte member 151 and cover the periphery thereof, and which has a size approximately the same as that of the spacer 145. An eighth through-hole conductor 18 is formed in a rear end portion of the alumina layer 154. The eighth through-hole conductor 18 electrically connects to the seventh through-hole conductor 17 formed in the spacer 145. The solid electrolyte member 151 of the oxygen-concentration detection cell 150 corresponds to the "first solid electrolyte member" of the invention.

The two electrodes 152, 153 respectively have porous electrode portions 152M, 153M mainly formed of platinum (Pt), and lead portions 152L, 153L. The electrode portions 152M, 153M are disposed on a first surface 151a (the upper surface in FIG. 4) and a second surface 151b (the lower surface in FIG. 4), respectively, of the solid electrolyte member 151. Of these electrode portions 152M, 153M, the electrode portion 152M disposed on the first surface 151a is exposed to the gas detection chamber 145c. The electrode 152 corresponds to the "first electrode" of the invention.

The lead portion 152L of the electrode 152 disposed on the first surface 151a is electrically connected to the electrode 138 of the oxygen pump cell 135 and the second electrode pad 126 through the sixth through-hole conductor 16 provided in the spacer 145. Meanwhile, the lead portion 153L of the electrode 153 disposed on the second surface 150b is electrically connected to the third electrode pad 127 via the eighth through-hole conductor 18 provided in the solid electrolyte member 151.

The heater element 160 includes first and second insulating members 161, 162, a heating resistor 163, and first and second heater lead portions 164, 165. Each of the first and second insulating members 161, 162 is a platelike member which is formed of alumina and which has a size similar to that of the detection element 130. The first and second insulating members 161, 162 sandwich the heating resistor 163 and the heater lead portions 164, 165 therebetween.

The heating resistor 163 is a heating element which is formed by a heating wire containing platinum as a main component and which has a meandering shape. The two heater lead portions 164, 165 are connected to opposite ends of the heating resistor 163 and extend rearward from the heating resistor 163. The heater element 160 corresponds to the "heater" of the invention, and the heating resistor 163 corresponds to the "heating portion" of the invention.

The first and second heater electrode pads 128, 129 are disposed on a rear end portion of the outer surface 162b of the second insulating member 162 such that the first and second heater electrode pads 128, 129 are arranged in parallel in the width direction of the heater element 160. First and second heater through-hole conductors 21 and 22 are formed in the second insulating member 162 at positions corresponding to the first and second heater electrode pads 128, 129. The first and second heater lead portions 164, 165 connected to the heating resistor 163 are electrically connected to the first and second heater electrode pads 128, 129 through the first and second heater through-hole conductors 21 and 22.

When the gas sensor 100 is operated, the heating temperature of the heater element 160 is controlled by an external heater control circuit (not shown). The heater element 160 heats the detection element 130 to several hundred degrees Celsius (e.g., 700 to 800° C.) to thereby activate the oxygen pump cell 135 and the oxygen-concentration detection cell 150.

The leakage portion 148 is formed in the spacer 145 such that it extends through the spacer 145 in the lamination direction and such that the leakage portion 148 is in direct contact with the two solid electrolyte members 136, 151 and the electrodes 138, 152 (more specifically, their lead portions 138L, 152L). More specifically, the leakage portion 148 is formed in the spacer 145 at a position shifted rearward from the opening which constitutes the gas detection chamber 145c such that the circumferential surface of the leakage portion 148 is covered by the spacer 145, and the top and bottom surfaces of the leakage portion 148 can contact the corresponding cells 135, 150.

The leakage portion 148 is mainly formed of zirconia. In the present embodiment, the expression "the leakage portion 148 is mainly formed of zirconia" means that the zirconia content of the leakage portion 148 is greater than 50 wt %. More preferably, the leakage portion 148 is formed such that its zirconia content falls within the range of 80 to 100 wt %.

Also, in order to facilitate joining between the leakage portion 148 and the spacer 145, the leakage portion 148 desirably contains an insulating ceramic, such as alumina, spinel, or titania ($TiO_2$), in an amount of 0 to about 20 wt %.

The gas sensor 100 of the present embodiment is subject to feedback control by a control circuit 200 (described below). During feedback control, the leakage portion 148 functions as a path through which electrons and/or oxygen ions move between the oxygen pump cell 135 and the oxygen-concentration detection cell 150. Thus, the leakage portion 148 suppresses oscillation of the control circuit 200 which performs feedback control on the basis of the sensor output. The mechanism in which the leakage portion 148 suppresses oscillation of the feedback control is described below in detail.

In the case of the gas sensor 100 of the present embodiment, the leakage portion 148 is disposed such that at least a portion of the leakage portion 148 overlaps the heating resistor 163 when the gas sensor element 120 is viewed in the lamination direction. Specifically, the leakage portion 148 is formed such that when the leakage portion 148 is imaginarily projected on the heating resistor 163 in the lamination direction as indicated by alternate long and short dashed lines in FIG. 4, at least a portion of its projection image is located on the heating resistor 163. Thus, the temperature of the leakage portion 148 is adequately controlled, and the electrical conductivity of the zirconia which constitutes the leakage portion 148 can be maintained at a satisfactory level. Therefore, oscillation of feedback control can be reliably suppressed, and fluctuation of the sensor output can be reliably suppressed.

Further, in the gas sensor 100 of the present embodiment, the leakage portion 148 is formed at a position determined such that the entire circumferential surface of the leakage portion 148 is covered by the spacer 145. This configuration prevents the outer surface of the leakage portion 148 from being exposed to exhaust gas. This configuration also prevents generation of a crack in the leakage portion 148, which crack would otherwise be generated when the leakage portion 148 is heated to a high temperature during operation of the gas sensor 100 and moisture contained in exhaust gas adheres to the outer surface of the heated leakage portion 148. Also, this configuration prevents adhesion of carbon to the outer surface of the leakage portion 148 which would otherwise result in electrical conduction between the leakage portion 148 and an eternal member via the metallic shell 110 or the like. Thus, blackening of the zirconia of the leakage portion 148 can be suppressed.

Preferably, the leakage portion 148 is formed such that its area measured on an arbitrary cross section taken perpendicular to the lamination direction is less than 50% the sum of the area of the spacer 145 and the area of the leakage portion 148 measured on that cross section. In the case where the area ratio of the leakage portion 148 of the spacer 145 is equal to or greater than the above-mentioned value, the current flowing through the leakage portion 148 (described below) becomes excessively large. That is, the function of the spacer 145 as an insulating layer in the gas sensor element 120 is impaired, and the measurement accuracy of the gas sensor 100 may degrade. Notably, in this case, the area of the spacer 145 does not include the area of the opening which forms the gas detection chamber 145c.

Figure 5:
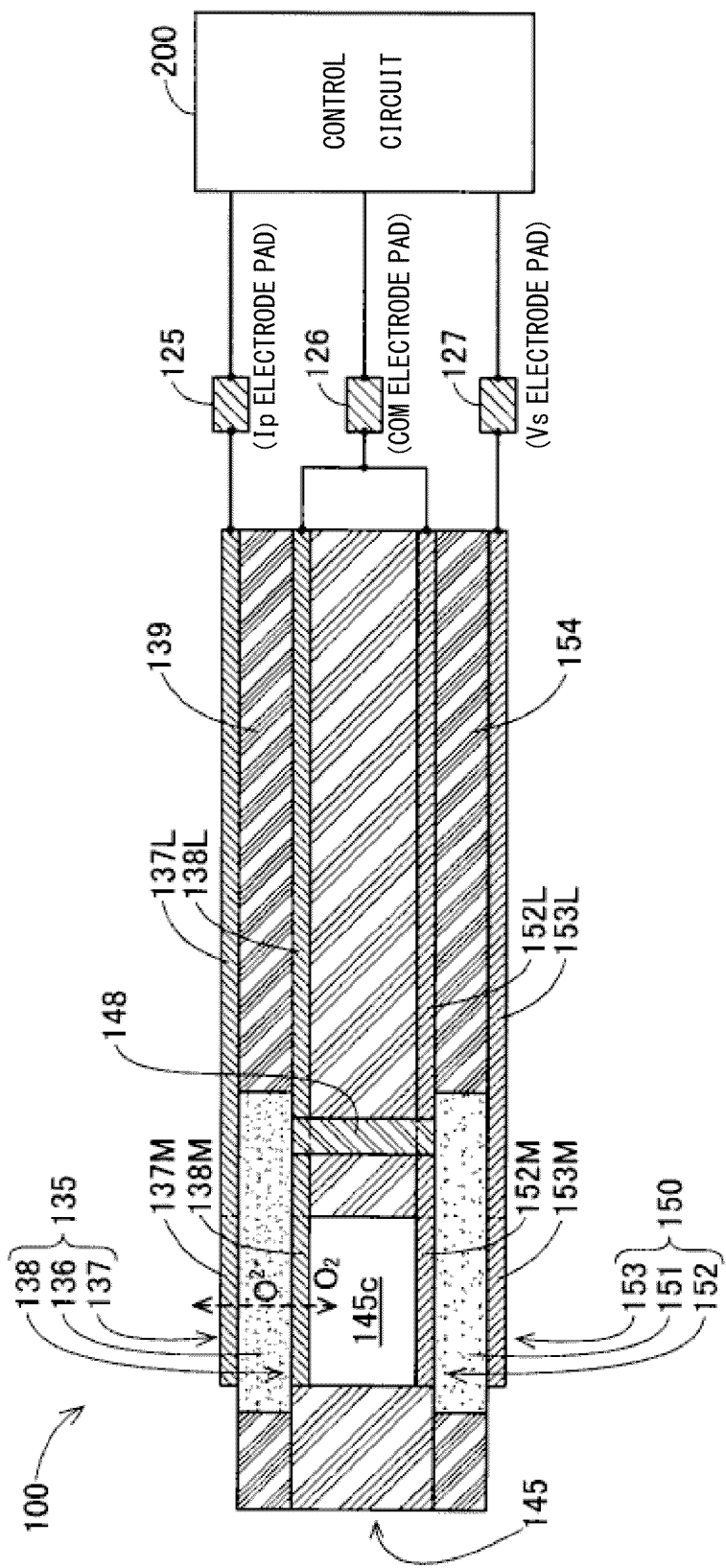
FIG. 5 is a schematic view showing a method of controlling the gas sensor.

FIG. 5 is a schematic view showing a method of controlling the gas sensor 100. Of the constituent elements of the gas sensor element 120, FIG. 5 schematically shows only the oxygen pump cell 135, the spacer 145, the oxygen-concentration detection cell 150, and the first to third electrode pads 125 to 127. FIG. 5 also shows the control circuit 200 which is provided externally of the gas sensor 100 and which is electrically connected to the oxygen pump cell 135 and the oxygen-concentration detection cell 150 through the first to third electrode pads 125 to 127.

As described above, in the case of the gas sensor element 120 of the gas sensor 100, when the spacer 145 is sandwiched between the two cells 135, 150, the gas detection chamber 145c is formed within the spacer 145. The electrode 138 of the oxygen pump cell 135 is disposed such that the electrode portion 138M faces the gas detection chamber 145c, and constitutes a portion of the wall surface of the gas detection chamber 145c.

Similarly, the electrode 152 of the oxygen-concentration detection cell 150 is disposed such that the electrode portion 152M faces the gas detection chamber 145c, and constitutes a portion of the wall surface of the gas detection chamber 145c. Notably, exhaust gas, which is a gas to be measured, is introduced into the gas detection chamber 145c through the diffusion limiting portions 146 (FIG. 4) provided in the spacer 145.

When a potential difference is produced across the electrodes 137, 138, oxygen ions move in the lamination direction through the solid electrolyte member 136 of the oxygen pump cell 135 in accordance with the potential difference. In the gas sensor 100, by supplying current from the control circuit 200 to the oxygen pump cell 135, oxygen is pumped into the gas detection chamber 145c and is pumped out of the gas detection chamber 145c through the solid electrolyte member 136. Notably, the oxygen pump cell 135 is also referred to as an "Ip cell".

In the solid electrolyte member 151 of the oxygen-concentration detection cell 150, when a difference in oxygen concentration exits between the first surface 151a side and that on the second surface 151b side, an electromotive force is generated in accordance with the concentration difference. In the gas sensor 100, the electromotive force between the electrodes 152, 153 of the oxygen-concentration detection cell 150 is detected so as to detect the oxygen concentration in the gas detection chamber 145c while using the oxygen concentration at the electrode portion 153M of the electrode 153 as a reference. The oxygen-concentration detection cell 150 is also referred to as an "electromotive force cell" or "Vs cell".

In the present specification, the first electrode pad 125 that is connected to the electrode 137 of the oxygen pump cell 135 is also referred to as an "Ip electrode pad 125." Also, the second electrode pad 126 connected to the electrode 138 of the oxygen pump cell 135 and the electrode 152 of the oxygen-concentration detection cell 150 is also referred to as a "COM electrode pad 126." Further, the third electrode pad 127 connected to the electrode 153 of the oxygen-concentration detection cell 150 is also referred to as a "Vs electrode pad 127."

The control circuit 200 performs the following feedback control for the gas sensor element 120. The control circuit 200 detects the output voltage Vs of the oxygen-concentration detection cell 150 via the COM electrode pad 126 and the Vs electrode pad 127. The control circuit 200 supplies a pump current Ip to the oxygen pump cell 135 via the Ip electrode pad 125 and the COM electrode pad 126 such that the output voltage of the oxygen-concentration detection cell 150 becomes equal to a predetermined reference value. In this manner, the control circuit 200 adjusts the oxygen concentration within the gas detection chamber 145c. The control circuit 200 outputs, as a result of detection by the gas sensor 100, a signal based on the value of the pump current supplied to the oxygen pump cell 135.

As described above, when the gas sensor 100 is operated, the electrode portion 153M of the electrode 153 of the oxygen-concentration detection cell 150 functions as a closed oxygen reference chamber having a reference oxygen concentration. In view of the above, when the gas sensor 100 is started, the control circuit 200 supplies a very small current (e.g., a current of about 15 µA) to the oxygen-concentration detection cell 150, to thereby introduce oxygen into the electrode portion 153M such that the oxygen concentration at the electrode portion 153M assumes a predetermined reference value.

When the gas sensor 100 is operated, the target value of the output voltage of the oxygen-concentration detection cell 150 is set to a value (e.g., about 450 mV) determined such that the air-fuel ratio of exhaust gas within the gas detection chamber 145c becomes equal to the stoichiometric air-fuel ratio. When the air-fuel ratio of the exhaust gas within the gas detection chamber 145c is lower than the stoichiometric air-fuel ratio (when the exhaust gas is rich), the control circuit 200 supplies a pump current to the oxygen pump cell 135 in a direction so as to pump oxygen into the gas detection chamber 145c. In contrast, when the air-fuel ratio of the exhaust gas within the gas detection chamber 145c is higher than the stoichiometric air-fuel ratio (when the exhaust gas is lean), the control circuit 200 supplies a pump current to the oxygen pump cell 135 in a direction so as to pump oxygen out of the gas detection chamber 145c.

Figure 6:
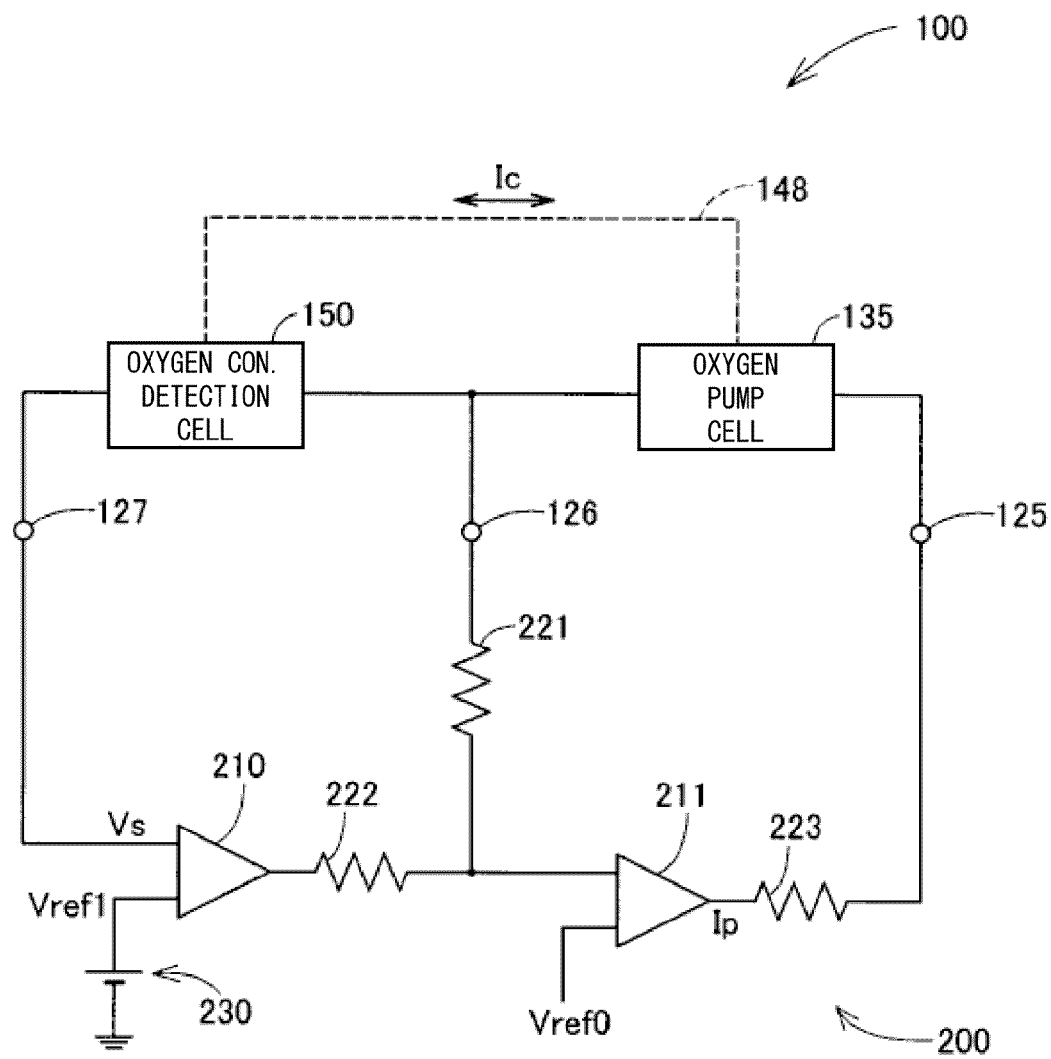
FIG. 6 is a schematic diagram showing an example of the configuration of a control circuit for the gas sensor.

FIG. 6 is a schematic view showing an example of the configuration of the control circuit 200 of the gas sensor 100. The control circuit 200 includes a PID (proportional, integral, and differential) element 210, an operational amplifier 211, first to third resistors 221 to 223, and a reference power supply 230. One input terminal of the PID element 210 is connected to the Vs electrode pad 127, and the other input terminal of the PID element 210 is connected to the reference power supply 230. The output terminal of the PID element 210 is connected to the COM electrode pad 126 through the first and second resistors 221, 222, and is connected to one input terminal of the operational amplifier 211 through the second resistor 222.

As described above, the COM electrode pad 126 and the PID element 210 are connected to one input terminal of the operational amplifier 211 through the first and second resistors 221, 222, respectively. A reference voltage Vref0 is applied to the other input terminal of the operational amplifier 211. The output terminal of the operational amplifier 211 is connected to the Ip electrode pad 125 through the third resistor 223.

In this control circuit 200, a signal corresponding to the difference between the reference voltage Vref1 output from the reference power supply 230 and the voltage Vs output from the oxygen-concentration detection cell 150 is output from the PID element 210 to the operational amplifier 211. Thus, a current corresponding to the output signal of the PID element 210 is supplied from the operational amplifier 211 to the oxygen pump cell 135 as a pump current.

Incidentally, in the case of a conventional laminate-type gas sensor in which an oxygen pump cell and an oxygen-concentration detection cell are stacked together as in the case of the gas sensor 100 of the present embodiment, the control circuit may oscillate when performing the above-described feedback control. The reason that such oscillation occurs is described below.

In the case of such a laminate-type gas sensor, when oxygen is pumped into the gas detection chamber or pumped out of the gas detection chamber by the oxygen pump cell such that the output voltage of the oxygen-concentration detection cell becomes equal to a target value, the output voltage of the oxygen-concentration detection cell changes with a time lag. This is because oxygen molecules require a finite time to move in the gas detection chamber between the oxygen pump cell and the oxygen-concentration detection cell.

If such a time lag is present, before the voltage of the oxygen-concentration detection cell reaches the target value, the pump current of the oxygen pump cell again changes on the basis of the voltage of the oxygen-concentration detection cell not having reached the target value. Accordingly, when the time lag becomes excessively large, the output voltage of the oxygen-concentration detection cell does not converge and the control circuit oscillates.

In contrast, in the gas sensor 100 of the present embodiment, the leakage portion 148 is provided between the oxygen pump cell 135 and the oxygen-concentration detection cell 150. This leakage portion 148 establishes electrical contact between the two cells 135, 150, to thereby suppress such a time lag. The mechanism of suppressing such a time lag is specifically described below.

Here, the air-fuel ratio of the exhaust gas within the gas detection chamber 145*c* is assumed to be lower than the stoichiometric air-fuel ratio. In such a case, oxygen is pumped into the gas detection chamber 145*c* by the oxygen pump cell 135. However, the electrode 152 of the oxygen-concentration detection cell 150 maintains a low oxygen concentration until the pumped-in oxygen reaches the electrode 152.

However, in the case of the gas sensor 100 of the present embodiment, when the pump current Ip changes, electrical transfer occurs, through the leakage portion 148, between the outer electrode 137 of the oxygen pump cell 135 and the electrode 152 of the oxygen-concentration detection cell 150 located on the side toward the gas detection chamber 145*c*. Specifically, when the pump current Ip changes, a portion of the pump current Ip flows (leaks) to the oxygen-concentration detection cell 150 through the leakage portion 148, and the output voltage Vs of the oxygen-concentration detection cell 150 changes to approach the target value.

As described above, in the gas sensor 100 of the present embodiment, an electrical change in the oxygen pump cell 135 is transferred to the oxygen-concentration detection cell 150 via the leakage portion 148, to thereby compensate for (reduce) a delay in change of the oxygen concentration at the oxygen-concentration detection cell 150. Thus, when the pump current Ip of the oxygen pump cell 135 changes, the output voltage of the oxygen-concentration detection cell 150 linearly reaches the target value more quickly, whereby generation of the above-described time lag is suppressed. This also applies to the case where the air-fuel ratio of the exhaust gas within the gas detection chamber 145*c* is higher than the stoichiometric air-fuel ratio, and oxygen is pumped out of the gas detection chamber 145*c* by the oxygen pump cell 135.

Figure 7:
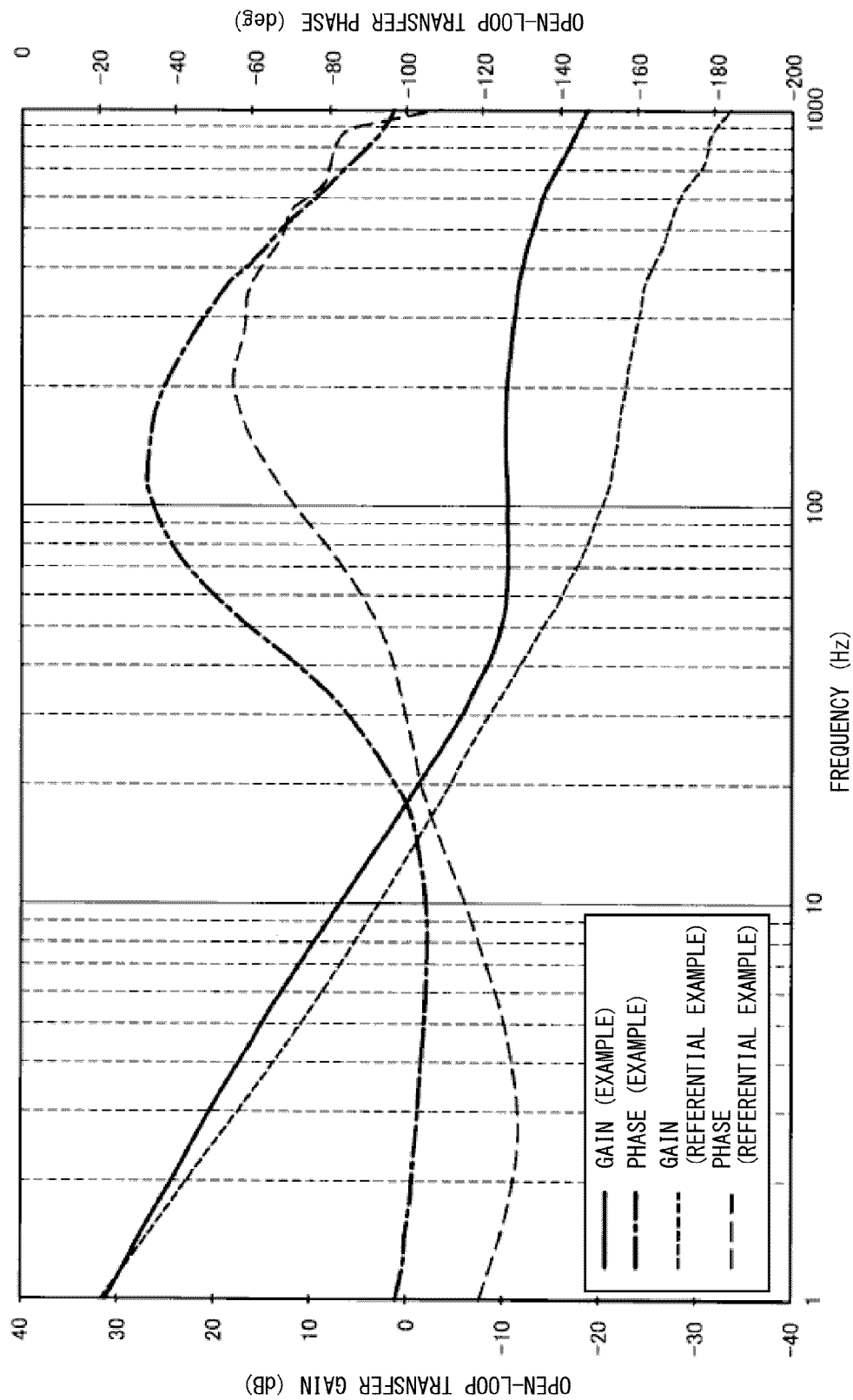
FIG. 7 is an explanatory graph showing the results of an experiment performed by the present inventors.

FIG. 7 is an explanatory graph showing the results of an experiment carried out to evaluate the performance of the gas sensor 100 of the present embodiment as an example. In the evaluation test, a voltage change within a predetermined range was periodically applied to the oxygen-concentration detection cell 150 as a disturbance. The ratio of an output voltage ΔVs (a change in the output voltage of the oxygen-concentration detection cell 150 caused by the disturbance) to a pump current ΔIp (a change in the pump current caused by the disturbance) was measured as the sensor gain, and the deviation of the phase of the output voltage ΔVs from the phase of the pump current ΔIp was measured as a sensor phase. Further, the ratio of the pump current ΔIp output from the control circuit 200 to the output voltage ΔVs input to the control circuit 200 was measured as a control circuit gain, and the deviation of the phase of the pump current ΔIp output from the control circuit 200 from the phase of the output voltage ΔVs input to the control circuit 200 was measured as a control circuit phase. The sum of the sensor gain and the control circuit gain was calculated as an open-loop transfer gain, and the sum of the sensor phase and the control circuit phase was calculated as an open-loop transfer phase.

In the graph of FIG. 7, the measurement results are plotted. In the graph, the horizontal axis represents the frequency of the disturbance, the left-hand vertical axis represents the open-loop transfer gain (dB), and the right-hand vertical axis represents the open-loop transfer phase (deg). Notably, in the graph of FIG. 7, measurement results are plotted in a similar evaluation test which was performed as a reference example using a gas sensor 100*a* and a control circuit 200*a*, described below.

Figure 8:
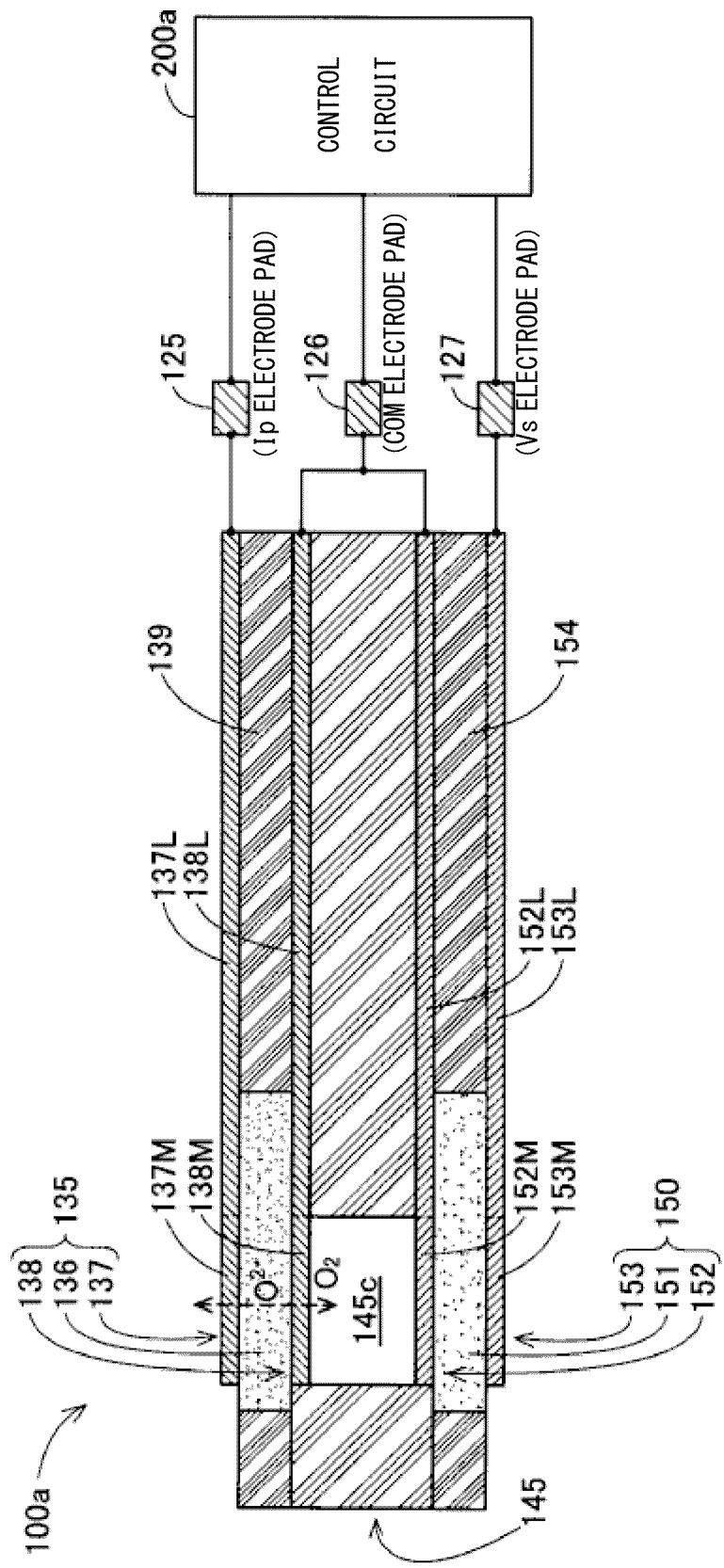
FIG. 8 is a schematic view showing the structure of a gas sensor serving as a reference example.

FIG. 8 is a schematic view showing the structure of the gas sensor 100*a* of the reference example. FIG. 8 is substantially the same as FIG. 5 except that the leakage portion 148 is not provided, and the control circuit 200*a* is provided in place of the control circuit 200. The structure of the gas sensor 100*a* of the reference example is identical to that of the gas sensor 100 of the present embodiment except for the leakage portion 148.

Figure 9:
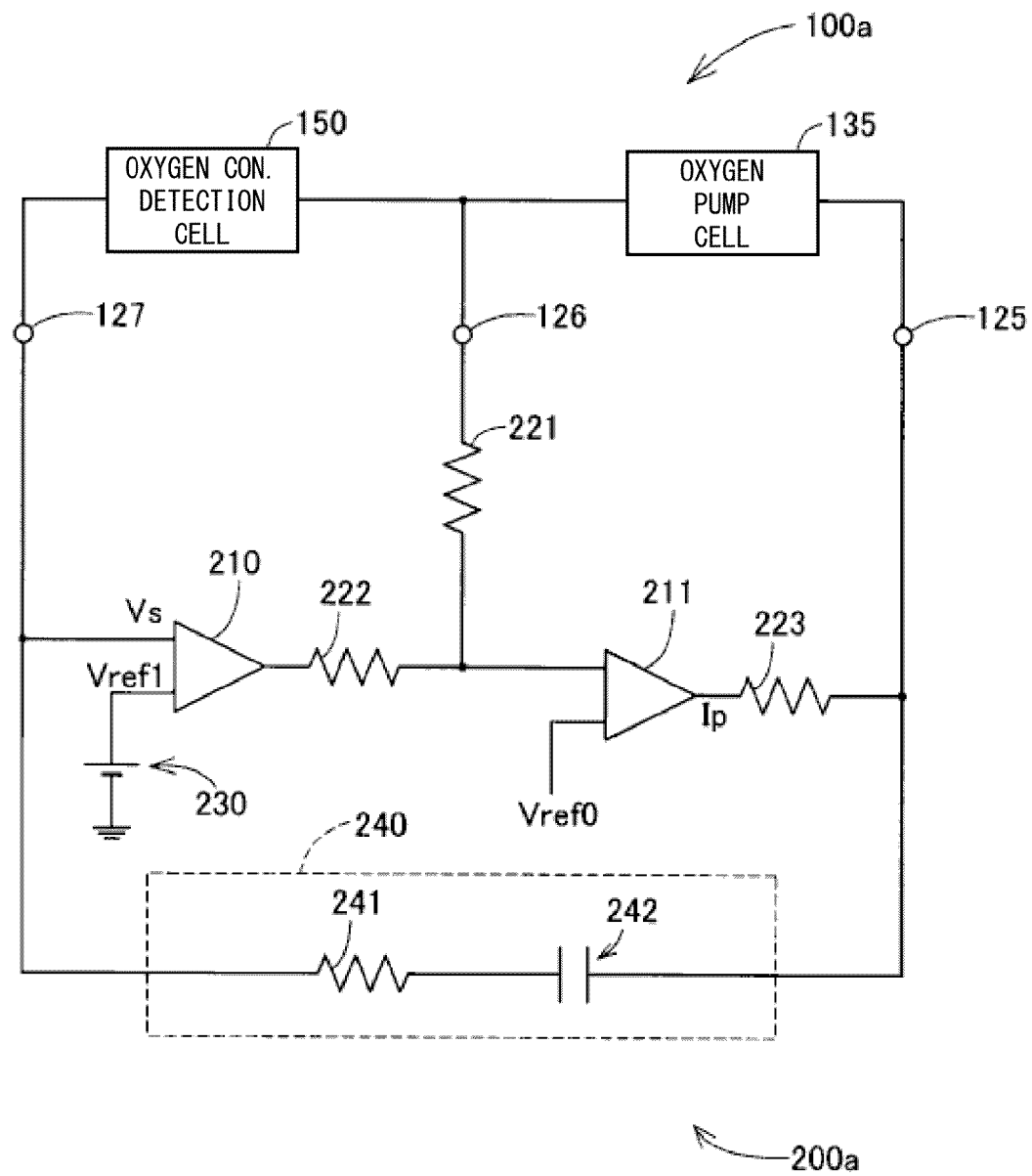
FIG. 9 is a schematic diagram showing an example of the configuration of a control circuit connected to the gas sensor of the reference example.

FIG. 9 is a schematic view showing an example of the configuration of the control circuit 200*a* connected to the gas sensor 100*a* of the reference example. FIG. 9 is substantially the same as FIG. 6 except that a high pass filter 240 is provided. The control circuit 200*a* performs feedback control for the gas sensor 100*a*. This feedback control is similar to that performed by the control circuit 200 used for the gas sensor 100 of the present embodiment. When the control circuit 200*a* performs feedback control, the control circuit 200*a* suppresses the occurrence of oscillation by the high pass filter 240 provided therein.

The high pass filter 240 includes a resistor 241 and a capacitor 242 connected in series. The resistor 241 side of the high pass filter 240 is connected to the Vs electrode pad 127, and the capacitor 242 side of the high pass filter 240 is connected to the Ip electrode pad 125. This high pass filter 240 allows current to flow therethrough in a predetermined amount only when the direction of the pump current flowing through the oxygen pump cell 135 changes. By using this predetermined amount of current flowing through the high pass filter 240, the control circuit 200*a* can mitigate a delay in voltage change of the oxygen-concentration detection cell 150 in relation to change in the pump current of the oxygen pump cell 135. Accordingly, oscillation of the control circuit 200*a* is suppressed.

In the case where the open-loop transfer phase becomes −180 (deg) or below when the open-loop transfer gain is 0 (dB) in the graph of FIG. 7, the control circuit oscillates. In the case where the open-loop transfer phase at the time when the open-loop transfer gain is 0 (dB) is greater than −180 (deg), the larger the amount by which the open-loop transfer phase is greater than −180 (deg), the greater the degree to which oscillation is suppressed.

The above performance evaluation test reveals the following. In the case where the gas sensor 100*a* and the control circuit 200*a* of the reference example are combined, the open-loop transfer phase becomes about −110 (deg) when the open-loop transfer gain is 0 (dB) (FIG. 7). Namely, in the case where the gas sensor 100*a* of the reference example is used, oscillation is suppressed by the control circuit 200*a* having the high pass filter 240.

In contrast, in the case of the gas sensor 100 of the present embodiment, the open-loop transfer phase becomes about −100 (deg) when the open-loop transfer gain is 0 (dB). Thus, in the case of the gas sensor 100 of the present embodiment, oscillation of the control circuit 200 is suppressed despite the control circuit 200 not including an oscillation suppression mechanism such as the high pass filter 240. This is because the leakage portion 148 functions as an oscillation suppression mechanism similar to that realized by the high pass filter 240 of the control circuit 200a.

As described above, according to the gas sensor 100 of the present embodiment, oscillation in feedback control is suppressed by providing the leakage portion 148, which electrically connects the oxygen pump cell 135 and the oxygen-concentration detection cell 150. Accordingly, when the pump current of the oxygen pump cell 135 is changed, the above configuration prevents the output voltage of the oxygen-concentration detection cell 150 from being greatly influenced, whereby fluctuation of the sensor output is suppressed.

In the case of the gas sensor 100 of the present embodiment, since the leakage portion 148 is provided, it is unnecessary to use the dedicated control circuit 200a which includes a constituent element for suppressing oscillation, such as the high pass filter 240 of the control circuit 200a of the reference example, which is composed of the resistor 241 and the capacitor 242. Accordingly, it is possible to insure compatibility of the control circuit with a gas sensor which is unlikely to cause the control circuit to oscillate and which avoids the necessity of providing the high pass filter 240 in the control circuit.

Conventionally, for a gas sensor of a type which is likely to cause oscillation of a control circuit, a dedicated control circuit has been used which includes a constituent element for suppressing oscillation as in the case of the control circuit 200a of the reference example. However, in the case of the gas sensor 100 of the present embodiment, such a constituent element for suppressing oscillation can be eliminated from the control circuit connected thereto. Since provision of such a constituent element in the control circuit is not required, cost can be reduced by an amount corresponding to the cost of including the constituent element.

In the gas sensor 100 of the present embodiment, the leakage portion 148, which electrically connects the oxygen-concentration detection cell 150 and the oxygen pump cell 135, is provided separately from the spacer 145, which is interposed between the oxygen-concentration detection cell 150 and the oxygen pump cell 135 so as to insulate the oxygen-concentration detection cell 150 from the oxygen pump cell 135. The occurrence of oscillation in feedback control can be suppressed by establishing an electrical connection between the two cells 150, 135. Therefore, the gas sensor 100 may be configured such that an electrical connection is established between the oxygen-concentration detection cell 150 and the oxygen pump cell 135 by interposing an electrically conductive layer between the two cells 150, 135 without providing the spacer 145 therebetween. However, if such a connection layer is provided, a large leakage voltage is produced due to leakage current flowing through the connection layer that is superimposed on the output voltage Vs of the oxygen-concentration detection cell 150. As a result, the measurement accuracy of the gas sensor 100 may decrease. In contrast, the gas sensor 100 is configured such that the spacer 145 is interposed between the oxygen-concentration detection cell 150 and the oxygen pump cell 135 and the leakage portion 148 is separately provided at a portion of the spacer 145. Therefore, the leakage voltage superimposed on the output voltage Vs of the oxygen-concentration detection cell 150 can be adequately suppressed. Accordingly, it is possible to suppress the occurrence of oscillation in feedback control, while preventing a reduction in the measurement accuracy of the gas sensor 100 which would otherwise occur due to the leakage current.

Figure 10:
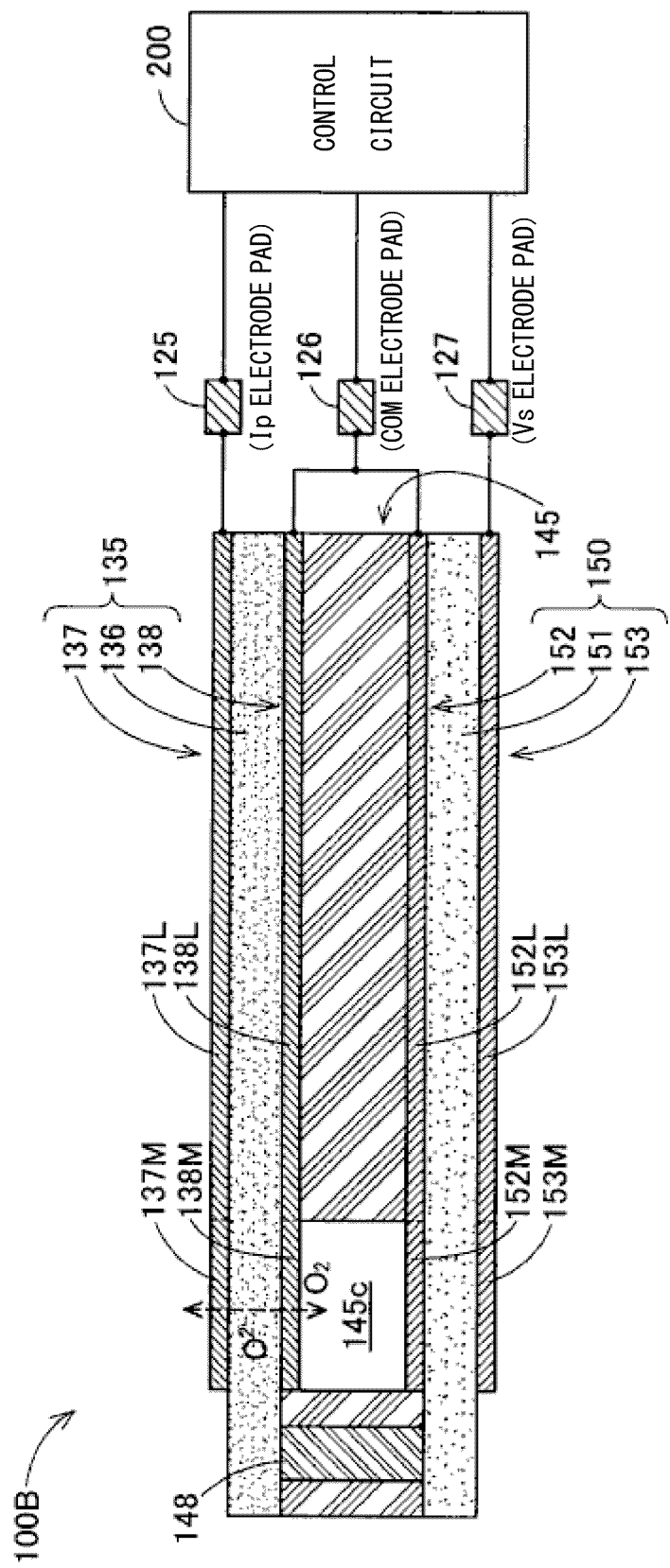
FIG. 10 is a schematic view for describing another structural example of the gas sensor.

B. Second Exemplary Embodiment:

FIG. 10 is a schematic view used for describing the structure of a gas sensor 100B which is another structural example of the gas sensor of the present invention. FIG. 10 is substantially the same as FIG. 5 except that the alumina layers 139 and 154 are omitted from the oxygen pump cell 135 and the oxygen-concentration detection cell 150 and that the leakage portion 148 is formed at a position different from the position of the leakage portion 148 in FIG. 5. In the gas sensor 100B of this structural example, the alumina layer 139 is eliminated from the oxygen pump cell 135, and the solid electrolyte member 136 of the oxygen pump cell 135 is formed as a platelike member having a size similar to that of the spacer 145. Similarly, the alumina layer 154 is eliminated from the oxygen-concentration detection cell 150, and the solid electrolyte member 151 of the oxygen-concentration detection cell 150 is formed as a platelike member having a size similar to that of the spacer 145. In this structural example, the leakage portion 148 penetrates a front end portion of the spacer 145 (located frontward of the gas detection chamber 145c) in the lamination direction, and is in direct contact with the solid electrolyte member 136 of the oxygen pump cell 135 and the solid electrolyte member 151 of the oxygen-concentration detection cell 150. Notably, the leakage portion 148 of this gas sensor 100B is separated from the electrodes 137, 138, 152, 153 of the cells 135, 150.

Even when the structure of this gas sensor 100B is employed, oscillation of feedback control is suppressed by the leakage portion 148. Also, since this configuration prevents the outer surface of the leakage portion 148 from coming into direct contact with exhaust gas, it is possible to prevent carbon or water droplets contained in exhaust gas from adhering to the outer surface of the leakage portion 148.

C. Modifications:

The present invention is not limited to the above-described embodiments, and may be practiced in various forms without departing from the scope of the invention. For example, the position and size of the leakage portion 148 are not limited to those described in the above embodiments. The leakage portion 148 may be formed at any position where the leakage portion 148 connects the oxygen pump cell 135 and the oxygen-concentration detection cell 150 so as to establish electrical conduction therebetween.

C1. Modification 1:

In the gas sensor 100 of the above-described embodiment, the leakage portion 148 is formed in a region which overlaps the heating resistor 163 of the heater element 160 when the gas sensor element 120 is viewed in the lamination direction. The leakage portion 148 may also be provided outside that region. However, forming the leakage portion 148 in such a region is preferred, because the temperature of the leakage portion 148 can be adequately controlled. Notably, the leakage portion 148 may be provided in a region near the heating resistor 163 which can be heated by the heating resistor 163.

C2. Modification 2:

In the above-described embodiment, the control circuit 200 is configured by combining the PID element 210 and the operational amplifier 211. However, the control circuit 200 may have a different configuration.

C3. Modification 3:

In the above-described embodiment, each of the oxygen pump cell 135 and the oxygen-concentration detection cell 150 is configured such that the paired electrodes 137, 138 or the paired electrodes 152, 153 are disposed on opposite surfaces of the first solid electrolyte member 136 or the second solid electrolyte member 151. However, each of the oxygen pump cell 135 and the oxygen-concentration detection cell 150 may be configured such that the paired electrodes 137, 138 or the paired electrodes 152, 153 are disposed on one surface of the first solid electrolyte member 136 or the second solid electrolyte member 151. In the above-described embodiment, the paired electrodes 137, 138 of the oxygen pump cell 135 and the paired electrodes 152, 153 of the oxygen-concentration detection cell 150 are disposed at approximately the same position in the longitudinal direction of the gas sensor element 120 (the direction of the axis AX). However, the paired electrodes 137, 138 of the oxygen pump cell 135 and the paired electrodes 152, 153 of the oxygen-concentration detection cell 150 may be disposed at respective positions which are shifted from each other in the longitudinal direction.

C4. Modification 4:

In the above-described embodiment, the gas sensor 100 detects the concentration of oxygen gas contained in a gas to be measured, through use of the oxygen-ion conductive solid electrolyte members 136, 151. However, the gas sensor 100 may be configured to detect the concentration of a gas other than oxygen.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2011-169070 filed Aug. 2, 2011 and based on Japanese Patent Application No. 2012-126737 filed Jun. 4, 2012, the disclosures of which are incorporated herein by reference in their entirety.

What is claimed is:

1. A gas sensor comprising:

a measurement chamber into which a gas to be measured can be introduced;

an oxygen-concentration detection cell including a plate-shaped first solid electrolyte member and a pair of electrodes disposed on the first solid electrolyte member, the oxygen-concentration detection cell being disposed adjacent to the measurement chamber such that at least a portion of a first electrode which is one of the electrodes of the oxygen-concentration detection cell faces the measurement chamber, the oxygen-concentration detection cell producing an output voltage corresponding to the concentration of oxygen within the measurement chamber;

an oxygen pump cell including a plate-shaped second solid electrolyte member and a pair of electrodes disposed on the second solid electrolyte member, the oxygen pump cell being disposed adjacent to the measurement chamber such that the oxygen pump cell faces the oxygen-concentration detection cell through the measurement chamber and such that at least a portion of a second electrode which is one of the electrodes of the oxygen pump cell faces the measurement chamber, the oxygen pump cell pumping oxygen into the measurement chamber and pumping oxygen out of the measurement chamber in accordance with a pump current supplied to the oxygen pump cell such that the output voltage of the oxygen-concentration detection cell becomes equal to a predetermined target voltage;

an insulating layer in which the measurement chamber is provided and which is interposed between and mechanically connects the first solid electrolyte member and the second solid electrolyte member so as to insulate the oxygen-concentration detection cell and the oxygen pump cell from each other; and a plate-shaped heater which is laminated on the second solid electrolyte member and in which a heating resistor is embedded, wherein:

the heating resistor has a meandering shape, a leakage portion which is mainly formed of zirconia and which mechanically and electrically connects the oxygen-concentration detection cell to the oxygen pump cell is disposed between the oxygen-concentration detection cell and the oxygen pump cell such that the leakage portion is located adjacent to the insulating layer;

the leakage portion is provided in a region which at least partially overlaps the heating resistor as viewed in the lamination direction of the gas sensor; and the leakage portion penetrates a portion of the insulating layer in the lamination direction of the gas sensor, the leakage portion being sandwiched between the first solid electrolyte member and the second solid electrolyte member.

2. The gas sensor as claimed in claim 1, wherein on at least one cross section of the insulating layer taken perpendicular to the lamination direction, the leakage portion has an area which is less than 50% the sum of the area of the insulating layer and the area of the leakage portion.

3. The gas sensor as claimed in claim 1, wherein the outer surface of the leakage portion is covered by the oxygen pump cell, the oxygen-concentration detection cell and the insulating layer.

* * * * *